US007374883B2

(12) United States Patent
Laue

(10) Patent No.: US 7,374,883 B2
(45) Date of Patent: May 20, 2008

(54) METHOD AND KIT FOR THE DETECTION OF A NOVEL CORONOAVIRUS ASSOCIATED WITH THE SEVERE ACUTE RESPIRATORY SYNDROME (SARS)

(75) Inventor: Thomas Laue, Bremen (DE)

(73) Assignee: QIAGEN Diagnostics GmbH, Hamburg (DE)

( * ) Notice: Subject to any disclaimer, the term of this patent is extended or adjusted under 35 U.S.C. 154(b) by 170 days.

(21) Appl. No.: 10/837,026

(22) Filed: Apr. 30, 2004

(65) Prior Publication Data

US 2005/0142536 A1 Jun. 30, 2005

Related U.S. Application Data

(60) Provisional application No. 60/467,117, filed on Apr. 30, 2003.

(51) Int. Cl.
*C12Q 1/68* (2006.01)
*C12P 19/34* (2006.01)
*C07H 21/02* (2006.01)

(52) U.S. Cl. ............ 435/6; 435/975; 435/91.1; 435/91.2; 536/23.1

(58) Field of Classification Search ............ None
See application file for complete search history.

(56) References Cited

U.S. PATENT DOCUMENTS 6,323,337 B1 11/2001 Singer et al.

FOREIGN PATENT DOCUMENTS

WO WO 00/58505 10/2000

OTHER PUBLICATIONS

Drosten et al. ("Identification of a Novel Coronavirus in Patients with Severe Acute Respiratory Syndrome" The New England Journal of Medicine. Apr. 10, 2003. pp. 1-10).*
Buck et al. ("Design Strategies and Performance of Custom DNA Sequencing Primers") BioTechniques. Sep. 1999. 27: pp. 528-536).*
Gelmini et al. ("Quantiative polymerase chain reaction-based homogeneous assay with fluorogenic probes to measure c-erbB-2 oncogene amplficiation" Clinical Chemisry. 1997. 43, 5: pp. 752-758).*
Mahony et al. "Performance and Cost evaluation of one commercial and six in-house conventional and real-time reverse transcription-pcr assays for detection of severe acute respiratory syndrome coronavirus" J Clin Microbiol. Apr. 2004;42(4):1471-6.*
New England Biolabs 1998/99 Catalog (NEB Catalog).*
Drosten et al., "Identification of a novel coronavirus in patients with severe acute repiratory syndrome," *N. Engl. J. Med.*, 348(20): 1967-76 (2003).
Ksiazek et al., "A novel Coronavirus Associated with Severe Acute Respiratory Syndrome," *N. Engl. J. Med.*, 348:1953-1966 (2003).
Marra et al., "The genome sequence of the SARS-Associated Coronavirus," *Science* 300:1399-1404 (2003).
Peiris et al., "Coronavirus as a possible cause of severe acute respiratory syndrome," *Lancet* 361:1319-1325, (2003).
Rota et al., "Characterization of a Novel Coronavirus Associated with Severe Acute Respiratory Syndrome," *Science* 300:1394-1399 (2003).
Ruan et al., "Comparative full-length genome sequence analysis of 14 SARS coronavirus isolates and common mutations associated with putative origins of infection," *Lancet* 361:1779-1785 (2003).
Yount et al., "Reverse genetics with a full-length infectious cDNA of severe acute respiratory syndrome coronavirus," *Proc. Natl. Acad. Sci.*, 100:12995-30000 (2003).

* cited by examiner

*Primary Examiner*—Kenneth R. Horlick
*Assistant Examiner*—Christopher M Babic
(74) *Attorney, Agent, or Firm*—Seed Intellectual Property Law Group

(57) ABSTRACT

The instant invention relates to a quantitative real time RT-PCR method for detecting Severe Acute Respiratory Syndrome-associated virus (SARS-associated virus) and to oligonucleotides and kits for detecting SARS-associated virus.

22 Claims, 17 Drawing Sheets

Figure 5

```
TACCGTAGAC TCATCTCTAT GATGGGTTTC AAAATGAATT ACCAAGTCAA  50
TGGTTACCCT AATATGTTTA TCACCCGCGA AGAAGCTATT CGTCACGTTC 100
GTGCGTGGAT TGGCTTTGAT GTAGAGGGCT GTCATGCAAC TAGAGATGCT 150
GTGGGTACTA ACCTACCTCT CCAGCTAGGA TTTTCTACAG GTGTTAACTT 200
AGTAGCTGTA CCGACTGGTT ATGTTGACAC TGAAAATAAC ACAGAATTCA 250
CCAGAGTTAA TGCAAAACCT CCACCAGGTG ACCAGTTTAA ACATCTTATA 300
```

$\lambda_{max,A}$: 651 nm  $\lambda_{max,E}$: 674 nm

D

Texas Red $\lambda_{max,A}$: 583 nm  $\lambda_{max,E}$: 603 nm

E

[Cl$_6$]: HEX    $\lambda_{max,A}$: 535 nm   $\lambda_{max,E}$: 556 nm
[Cl$_4$]: TET    $\lambda_{max,A}$: 521 nm   $\lambda_{max,E}$: 536 nm

F

JOE $\lambda_{max,A}$: 527 nm   $\lambda_{max,E}$: 548 nm

G edans $\lambda_{max,A}$: 336 nm $\lambda_{max,E}$: 490 nm

H dabcyl $\lambda_{max,A}$: 453 nm

I

ROX (6-ROX)

ROX: $\lambda_{max,A}$: 568 nm $\lambda_{max,E}$: 595 nm
6-ROX: $\lambda_{max,A}$: 575 nm $\lambda_{max,E}$: 602 nm

J

TAMRA

$\lambda_{max,A}$: 555 nm $\lambda_{max,E}$: 580 nm

K

Fluorescein $\lambda_{max,A}$: 494 nm  $\lambda_{max,E}$: 525 nm

L

6 - FAM $\lambda_{max,A}$: 492 nm  $\lambda_{max,E}$: 515 nm

M rhodamine 6G
$\lambda_{max,A}$: 518 nm  $\lambda_{max,E}$: 543 nm

N

CY3
$\lambda_{max,A}$: 552 nm  $\lambda_{max,E}$: 565 nm

O

| A (nm) | E (nm) | Farbstoffe |
|---|---|---|
| 349 | 448 | AMCA |
| 336 | 490 | ADANS |
| 495 | 503 | BODIPY 493/503 |
| 505 | 513 | BODIPY LF |
| 494 | 515 | 6-FAM, Fluorescein |
| 496 | 516 | 6-OREGON Green 488 |
| 521 | 536 | TET |
| 518 | 543 | Rhodamin 6G (6-R6G) |
| 531 | 545 | BODIPY FL Br2 |
| 528 | 547 | BODIPY R6G |
| 527 | 548 | 6-JOE |
| 535 | 552 | BODIPY 530/550 |
| 535 | 555 | HEX |
| 552 | 565 | Cy3 |
| 559 | 569 | BODIPY 558/568 |
| 542 | 574 | BODIPY TMR 542/574 |
| 546 | 579 | 5-TAMRA |
| 560 | 580 | NED |
| 575 | 602 | 6-ROX |
| 583 | 603 | TEXAS Red |
| 588 | 616 | BODIPY TR 589/617 |
| 630 | 640 | Light Cycler RED 640 |
| 625 | 640 | BODIPY 630/650 |
| 646 | 660 | BODIPY 650/665 |
| 651 | 674 | Cy5 |
| 700 | 710 | Light Cycler Red |
| 678 | 703 | Cy 5.5 |
| 685 | 705 | IRD 700 |
| 685 | 705 | La Jolla Blue |
| 743 | 767 | Cy 7 |
| 787 | 807 | IRD 41 |

A = Absorption
E = Emission

SEQUENCE LISTING

<160> NUMBER OF SEQ ID NOS: 4

<210> SEQ ID NO 1
<211> LENGTH: 300
<212> TYPE: DNA
<213> ORGANISM: Human-Pneumonia Associated Coronavirus

<400> SEQUENCE: 1

```
taccgtagac tcatctctat gatgggtttc aaaatgaatt accaagtcaa tggttaccct      60
aatatgttta tcacccgcga agaagctatt cgtcacgttc gtgcgtggat tggctttgat     120
gtagagggct gtcatgcaac tagagatgct gtgggtacta acctacctct ccagctagga     180
ttttctacag gtgttaactt agtagctgta ccgactggtt atgttgacac tgaaaataac     240
```

```
acagaattca ccagagttaa tgcaaaacct ccaccaggtg accagtttaa acatcttata    300

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ccgcgaagaa gctattcgtc                                                20

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
gtaggttagt acccacagca tctctagt                                       28

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
tcgtgcgtgg attggctttg atgt                                           24
```

METHOD AND KIT FOR THE DETECTION OF A NOVEL CORONOAVIRUS ASSOCIATED WITH THE SEVERE ACUTE RESPIRATORY SYNDROME (SARS)

This application claims the benefit of priority of U.S. Provisional application Ser. No. 60/467,117, filed Apr. 30, 2003, the entire contents of which is incorporated herein by reference.

The present invention relates generally to the field of medicine and more specifically to infectious diseases.

Severe Acute Respiratory Syndrome (SARS) is a disease that emerged in Asia and resulted in an epidemic that had devastating health and economic effects. The disease spread rapidly from infected patient to infected patient, including numerous health care workers. Because the disease is so infectious, it is important to develop diagnostic methods to allow rapid diagnosis of this highly infectious disease.

SARS-associated virus, tentatively named HPAC (Human Pneumonia-Associated Coronavirus), has recently been identified by Drosten et al., and a qualitative real time RT-PCR (reverse transcriptase polymerase chain reaction) has been disclosed (Drosten et al. (2003) "Identification of a novel Coronavirus in patients with Severe Acute Respiratory Syndrome." *N. Engl. J. Med.* 348:1967-1976 (2003)).

Thus, there exists a need to develop rapid methods for diagnosing SARS. The present invention satisfies this need and provides related advantages as well.

SUMMARY OF THE INVENTION

The instant invention relates to an efficient, sensitive and reliable quantitative real time RT-PCR method for detecting Severe Acute Respiratory Syndrome-associated virus (SARS-associated virus), to oligonucleotides and kits for detecting SARS-associated virus.

BRIEF DESCRIPTION OF THE DRAWINGS

FIG. 5 shows a protocol for amplification of the cDNA.

FIG. 9 shows the nucleotide sequence (SEQ ID NO:1) of SARS associated viruses (BNI-1).

FIG. 10 shows the structure of exemplary fluroescent dyes. FIG. 100 shows absorption and emission wavelenths for various fluorescent dyes.

DETAILED DESCRIPTION OF THE INVENTION

Figure 1:
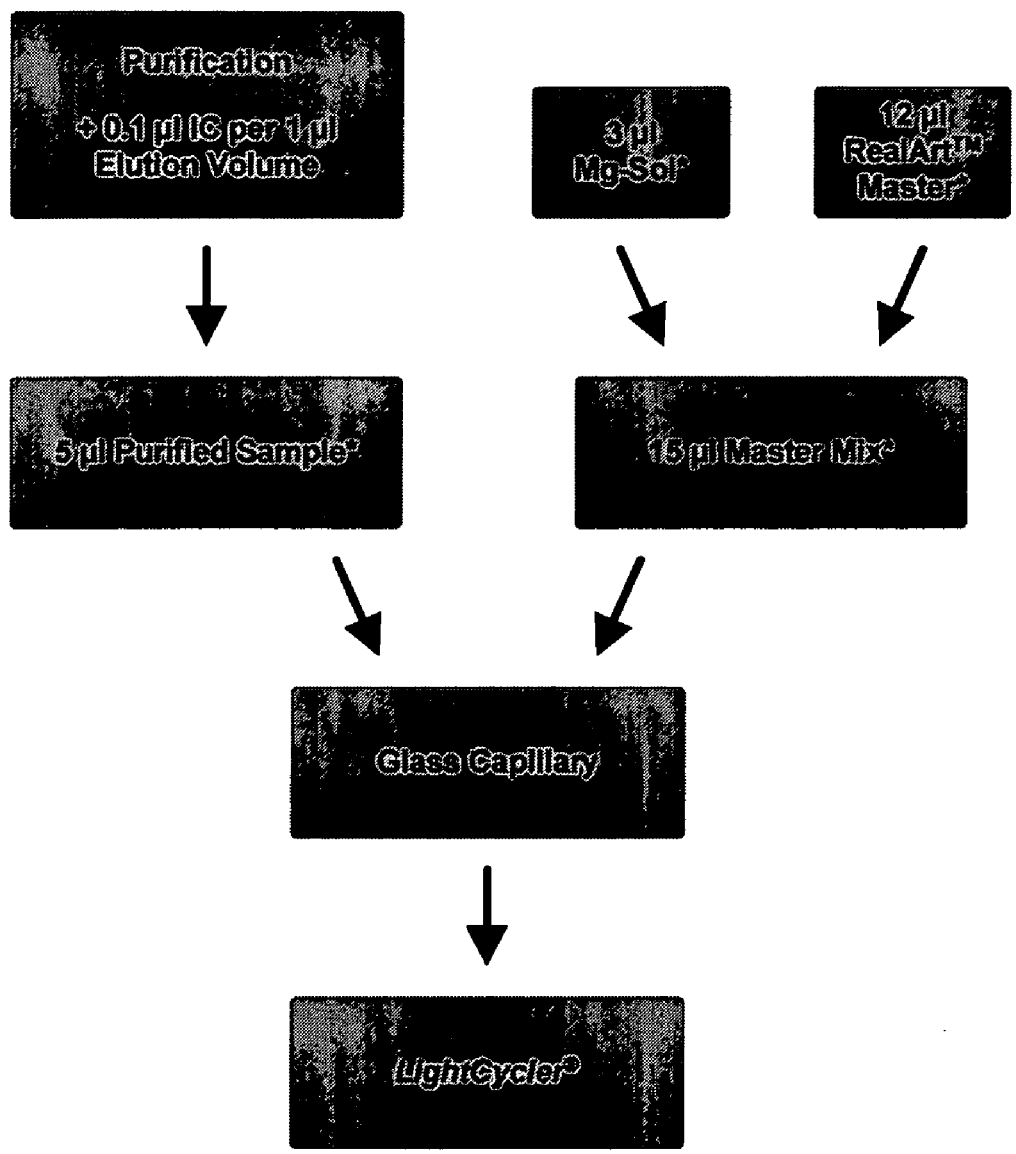
FIG. 1 shows a schematic workflow for the control of both the purification procedure and PCR inhibition.

The invention relates to a method for detecting Severe Acute Respiratory Syndrome-associated virus (SARS-associated virus), named HPAC (Human Pneumonia-Associated Coronavirus), wherein a real time RT-PCR reaction is performed using a biological sample. Based on the sequence data an efficient, sensitive and reliable quantitative real time RT PCR method was developed. In one embodiment, the forward primer has a length of approximately 18 to 31 nucleotides and binds to a region defined by nucleotides 69 to 98 of the sequence shown as SEQ ID NO:1; and wherein the reverse primer has a length of approximately 18 to 31 nucleotides and binds to a region defined by nucleotides 123 to 168 of the sequence shown as SEQ ID NO:1; and wherein the probe has a length of approximately 18 to 35 nucleotides and binds to a region defined by nucleotides 89 to 132 of the sequence shown as SEQ ID NO:1; and wherein the probe is labeled with two dyes, one dye of which is a fluorescent reporter dye, and one dye of which is a quencher dye, and wherein at least one dye is a fluorescent dye; and the SARS virus is detected by detection of real time fluorescence, if amplification of virus specific sequence occurs.

In an additional embodiment, the invention provides a method for detecting Severe Acute Respiratory Syndrome-associated virus (SARS-associated virus), named HPAC (Human Pneumonia-Associated Coronavirus). The method can include the steps of contacting a biological sample with a set of primers and a probe, incubating under conditions allowing amplification of nucleic acid using the primers, and determining binding of the probe to amplified nucleic acid, wherein detecting binding of the probe to amplified nucleic acid indicates the presence of SARS-associated virus, wherein the forward primer has a length of approximately 18 to 31 nucleotides and binds to a region defined by nucleotides 69 to 98 of the sequence shown as SEQ ID NO:1; and wherein the reverse primer has a length of approximately 18 to 31 nucleotides and binds to a region defined by nucleotides 123 to 168 of the sequence shown as SEQ ID NO:1; and wherein the probe has a length of approximately 18 to 35 nucleotides and binds to a region defined by nucleotides 89 to 132 of the sequence shown as SEQ ID NO:1; and wherein the probe is labeled with two dyes, one dye of which is a fluorescent reporter dye, and one dye of which is a quencher dye, and wherein at least one dye is a fluorescent dye. The method can be performed using real time RT-PCR.

In yet another embodiment, the invention provides a method for detecting Severe Acute Respiratory Syndrome-associated virus (SARS-associated virus), named HPAC (Human Pneumonia-Associated Coronavirus). The method can include the steps of contacting a biological sample with a set of primers and a probe, incubating under conditions allowing amplification of nucleic acid using the primers, and determining binding of the probe to amplified nucleic acid, wherein detecting binding of the probe to amplified nucleic indicates the presence of SARS-associated virus, wherein the forward primer has a length of approximately 18 to 35 nucleotides and binds to a region defined by nucleotides about 1 to about 240 of the sequence shown as SEQ ID NO:1; and wherein the reverse primer has a length of approximately 18 to 35 nucleotides and binds to a region defined by nucleotides about 60 to about 300 of the sequence shown as SEQ ID NO:1; and wherein the probe has a length of approximately 12 to 40 nucleotides and binds to a region defined by nucleotides about 21 to about 279 of the sequence shown as SEQ ID NO:1; and wherein the probe is labeled with two dyes, one dye of which is a fluorescent reporter dye, and one dye of which is a quencher dye, and wherein at least one dye is a fluorescent dye.

The forward primer may bind to a region of SEQ ID NO:1 from approximately nucleotide 1 to approximately nucleotide 240. The reverse primer may bind to a region of SEQ ID NO:1 from approximately nucleotide 60 to approximately nucleotide 300. The probe may thus bind to a region between approximately nucleotide 21 to approximately nucleotide 279 of SEQ ID NO:1. Generally, it is useful to obtain an amplification product that is at least an 80 mer.

In another embodiment, the forward primer has a length of approximately 18 to 35 nucleotides and binds to a region defined by nucleotides about 1 to about 240 of the sequence shown as SEQ ID NO:1; and wherein the reverse primer has a length of approximately 18 to 35 nucleotides and binds to a region defined by nucleotides about 60 to about 300 of the sequence shown as SEQ ID NO:1; and wherein the probe has a length of approximately 12 to 40 nucleotides and binds to a region defined by nucleotides about 21 to about 279 of the sequence shown as SEQ ID NO:1; and wherein the probe is labeled with two dyes, one dye of which is a fluorescent reporter dye, and one dye of which is a quencher dye, and wherein at least one dye is a fluorescent dye; and the SARS virus is detected by detection of real time fluorescence, if amplification of virus specific sequence occurs.

In a specific embodiment, the forward primer has the sequence shown as SEQ ID NO:2, the reverse primer has the sequence shown as SEQ ID NO:3, and wherein the probe has the sequence shown as SEQ ID NO:4.

Particularly useful binding regions within SEQ ID NO:1 range from approximately nucletoide 30 to approximately nucleotide 100 (region A), approximately nucleotide 120 to approximately nucleotide 170 (region B), and approximately nucleotide 230 to approximately nucleotide 270 (region C). Thus, forward and reverse primers may be selected from any selection of the regions A, B and C, that is, if forward and reverse primers bind within ranges A and B, the probe would have to bind "in between", that is, to the thus amplified sequence. Also possible are primer combinations A+C or B+C, which determine the sequence range where the probe would bind.

The length of the primers may vary between approximately 18 and approximately 35 nucleotides, or any specific value within said range. According to a particular embodiment, the primers have a length of between approximately 18 to 31 nucleotides and bind within a range from nucleotide 69 to nucleotide 98, or from nucleotide 123 to nucleotide 168.

The length of the probe may vary between approximately 12 and 40 nucleotides, or any specific value within said range useful for detecting the amplified sequence.

Further, it will be possible to perform the method using the minor groove binding principle, where the length of the probe may be as short as approximatley 12 nucleotides.

According to another embodiment, it will be possible to combine two probes (for example one probe having a length of approximately 12 nucleotides and one having about 6-7 nucleotides), if the method is performed according to the LightCycler principle, where light harvester and quencher dyes are used on the probes. This method is well known to a person skilled in the art. Alternatively, probes can be used in accordance with the quenched FRET principle which is disclosed in Krupp et al.: Nucleic acid preparations of pathogens from biological samples for real-time PCR analysis. In Nucleic Acids Isolation Methods (Bowien, B. & Dürre, P., eds.). American Scientific Publishers, Stevenson Ranch, 2002.

The following individual primers are specifically excluded from individual primers of the invention: (1) primer binding to region from nucleotide 68 to nucleotide 87 of SEQ ID NO:1 (corresponding to BNITMS1 in Drosten et al.); (2) primer binding to region from nucleotide 82 to nucleotide 101 of SEQ ID NO:1 (corresponding to BNIinS in Drosten et al.); (3) primer binding to region from nucleotide 34 to nucleotide 57 of SEQ ID NO:1 (corresponding to BNIoutS2 in Drosten et al.); (4) primer binding to region from nucleotide 124 to nucleotide 145 of SEQ ID NO:1 (corresponding to BNITMAs2 in Drosten et al.); (5) primer binding to region from nucleotide 169 to nucleotide 190 of SEQ ID NO:1 (corresponding to BNIinAs in Drosten et al.); and (6) primer binding to region from nucleotide 203 to nucleotide 223 of SEQ ID NO:1 (corresponding to BNIoutAs in Drosten et al.).

Further, with respect to methods of the invention and primer pairs of the invention, the specific combination of (1) and (4), (2) and (5), as well as (3) and (6) of the specifically excluded primers described above are also specifically excluded from primer pairs of the invention and from methods of the invention using such primer pairs. However, it is understood that individual primers (1) to (6) can be used as part of a primer pair with another primer that is not primers (1) to (6), if desired, for use in methods of the invention.

According to a particular embodiment, the reporter dye is FAM, 6-FAM, 5-FAM and ALEXA-288. According to a further embodiment, the quencher dye is TAMRA, DABCYL or QSY. Exemplary fluorscent dyes are shown in FIG. 10. Exemplary fluorescent dyes are well known in the art (see, for example, U.S. Pat. No. 6,323,337; WO 00/58505 (PCT/EP99/07127) and references citd therein, Hermanson, *Bioconjugate Techniques*, Academic Press, San Diego (1996), each of which is incorporated herein by reference).

The detection method is either a qualitative or a quantitative method. Specifically, the detection is a quantitative detection of the real time fluorescence signal intensity.

The biological sample used for detecting SARS-associated virus is a body fluid, and more specifically sputum, feces or blood.

The advantage of the present invention is that for the first time, quantitative detection of SARS-associated virus became possible with the theoretical detection limit of 10 genome equivalents in PCR, corresponding to 120 copies of RNA per ml biological sample. The RT-PCR method according to the instant invention is positive in at least 95% of tested cases.

The PCR efficiency essentially corresponds to the theoretical value of 2. More particularly, the efficiency is at least approximately 1.9. It is noteworthy that the method disclosed by Drosten et al. shows a significantly lower efficiency, and a detection limit of more than 100 genome equivalents in PCR.

The instant invention thus provides for the first time an efficient, sensitive and reliable quantitative real time RT-PCR method for detecting Severe Acute Respiratory Syndrome-associated virus (SARS-associated virus).

The instant invention further relates to a kit for performing the above-mentioned method for detecting Severe Acute Respiratory Syndrome-associated virus (SARS-associated virus). Specifically, the kit is a kit for detecting SARS-associated virus through real time RT-PCR, comprising a forward primer having a length of approximately 18 to 31 nucleotides, which forward primer binds to a region defined by nucleotides 69 to 98 of the sequence shown as SEQ ID NO:1; a reverse primer having a length of approximately 18 to 31 nucleotides, which reverse primer binds to a region defined by nucleotides 123 to 168 of the sequence shown as SEQ ID NO:1; and a probe having a length of approximately 18 to 35 nucleotides, which probe binds to a region defined by nucleotides 89 to 132 of the sequence shown as SEQ ID NO:1; and wherein the probe is labeled with two dyes, one dye of which is a fluorescent reporter dye, and one dye of which is a quencher dye, and wherein at least one dye is a fluorescent dye.

According to a specific embodiment of the invention, the kit comprises a forward primer having the sequence shown as SEQ ID NO:2, a reverse primer having the sequence shown as SEQ ID NO:3, and a probe having the sequence shown as SEQ ID NO:4.

According to a particular embodiment, the reporter dye is FAM, 6-FAM, 5-FAM and ALEXA-288. According to a further embodiment, the quencher dye is TAMRA, DABCYL or QSY.

It is well understood by a person skilled in the art that a kit of the invention may further comprise enzymes and reagents required for performing a real time RT-PCR reaction.

The invention also relates to oligonucleotides having a length of approximately 18 to 31 nucleotides, which binds to a region defined by nucleotides 69 to 98 of the sequence shown as SEQ ID NO:1. Specifically, the oligonucleotide has the sequence shown as SEQ ID NO:2. The invention also relates to oligonucleotides having a length of approximately 18 to 35 nucleotides, which binds to a region defined by nucleotides 1 to 240 of the sequence shown as SEQ ID NO:1.

The invention also relates to oligonucleotides having a length of approximately 18 to 31 nucleotides, which binds to a region defined by nucleotides 123 to 168 of the sequence shown as SEQ ID NO:1. Specifically, the oligonucleotide has the sequence shown as SEQ ID NO:3. The invention also relates to oligonucleotides having a length of approximately 18 to 35 nucleotides, which binds to a region defined by nucleotides 60 to 300 of the sequence shown as SEQ ID NO:1.

The invention additionally provides methods of determining the presence of SARS-associated virus or HPAC using the methods disclosed herein. The invention also provides such methods for determining the presence of HPAC and further including the step of reporting the result of said determination.

The following examples are intended to illustrate but not to limit the present invention.

EXAMPLE 1

Isolation of Viral RNA and PCR Conditions

Isolation of the viral RNA

Extraction of the nucleic acid is performed with the QIAamp Viral RNA Mini Kit (QIAGEN, 52904) or QIAamp Ultrasens Virus Kit (QIAGEN, 53704). As an advantage of the Ultrasens Kit, it is possible to use 1000 µl sample volume (instead of 200 µl with the Mini Kit), and in both cases, the nucleic acid is eluted in a volume of 60 µl. Using 5 µl eluate in 20 µl PCR reaction, a larger aliquot of the sample (1/12 of 1000 µl is equivalent to 83 µl sample, instead of 1/12 of 200 µl, equivalent to 17 µl sample) can be analysed for the presence of viral RNA.

LightCycler™ PCR

Amplification and detection of HPAC is performed by Real-Time RT-PCR in a LightCycler instrument. Specificity of the PCR detection is based on the use of HPAC-specific primers and a fluorescent, double-labelled oligonucleotide probe. The probe sequence is located within the primer-defined HPAC-amplicon.

This set-up enables the use of fluorescence measurements for direct quantitative and specific detection of HPAC-specific DNA amplification inside the closed PCR-reaction vessel. The technology used in this step is based on the 5'-exonuclease assay, as defined in U.S. Pat. Nos. 5,210,015 and 5,487,972. Basics and applications of this technology are readily available in scientific publications, for example in Krupp et al., Nucleic acid preparations of pathogens from biological samples for real-time PCR analysis. In *Nucleic Acids Isolation Methods* (Bowien, B. & Dürre, P., eds.). American Scientific Publishers, Stevenson Ranch, 2002.

Selection of the sequences of the primers and of the hybridization probe. Two criteria have to be met. Inclusivity: all known variants of HPAC have to be detected. Specificity: All other, closely related Coronaviridae have to be excluded.

Based on a published, detailed sequence alignment (Drosten et al., *N. Engl. J. Med.* 348:1967-1976 (2003) which is incorporated herein by reference), the following primers were chosen:

Sense

```
5' CCG CGA AGA AGC TAT TCG TC 3';    (SEQ ID NO:2)
```

(20 nt; Position 75-94)

Antisense

```
5' GTA GGT TAG TAC CCA GAG CAT CTC   (SEQ ID NO:3)
TAG T 3';
```

(28 nt; complementary to position 139-166)

The probe sequence was chosen, as published by Drosten et al.:

Probe BNITMP

```
5' (6-FAM) TCG TGC GTG GAT TGG CTT   (SEQ ID NO:4)
TGA TGT (dabcyl) 3';
```

(24 nt; Position 99-122)

The probe was labelled with a reporter dye (here 6-FAM) at the 5'-end and with a quencher dye (preferred is a non-fluorescent quencher like dabcyl) at the 3'-end. As known in the art, this probe oligonucleotide is blocked at the 3'-end to prevent enzymatic elongation. This elongation would result in a longer hybridization sequence, which could result in less specific hybridization with related, non-desired sequences.

Experimental protocol for performing HPAC detection with the LightCycler instrument Table 1 shows exemplary reaction conditions. The following or similar reaction conditions can be used:

TABLE 1

Reaction conditions

| Component | Volume(μl) |
|---|---|
| 2 × RT/Taq reaction buffer | 10 |
| MgSO$_4$ (100 mM) | 1-3 |
| BSA | 1-2 |
| Sense-Primer (100 μM) | 0.1-0.5 |
| Antisense-Primer (100 μM) | 0.2-1 |
| Probe (30 μM) | 0.1-0.5 |
| IC-Sense-Primer (100 μM) | 0.1-0.5 |
| IC-Antisense-Primer (100 μM) | 0.1-0.5 |
| IC-JOE-Sonde (30 μM) | 0.1-0.5 |
| IC-LCR-705-Sonde (30 μM) | 0.1-0.5 |
| IC-Template (RNA) | 0.1-0.5 |
| Platinum-Taq | 0.1-0.3 |
| RT/Taq-Mix | 1 |
| HPAC-RNA or nucleic acid extracted from the unknown sample | 5 |
| H$_2$O | add 20 μl |

Table 2 shows an exemplary program for use in the Light-Cycler:

TABLE 2

Light Cycler Program

| Program | Temperature [° C.] | Time [sec] | Slope [° C./sec] | 2nd Target Temperature [° C.] | Step Size | Step Delay | Acquisition |
|---|---|---|---|---|---|---|---|
| Reverse Transcription | | | | | | | |
| 1 | 50 | 600 | 20 | 0 | 0 | 0 | none |
| Denaturation | | | | | | | |
| 1 | 95 | 10 | 20 | 0 | 0 | 0 | none |
| Amplification (50 cycles) | | | | | | | |
| 1 | 95 | 2 | 20 | 0 | 0 | 0 | none |
| 2 | 55 | 12 | 20 | 0 | 0 | 0 | single |
| 3 | 72 | 10 | 5 | 0 | 0 | 0 | none |
| Cooling | | | | | | | |
| 1 | 40 | 30 | 20 | 0 | 0 | 0 | none |

Sensitivity of HPAC Detection

A PCR-derived construct was used that combines the HPAC amplicon sequence with the promoter sequence for T7 RNA polymerase. In a dilution series, the detection limit of 120 HPAC genome equivalents per ml sample was determined, equivalent to 10 genome equivalents per 50 μl PCR reaction.

Kit Components

All required materials, including positive controls (in vitro transcript of HPAC-RNA) and internal control, IC (in vitro transcript with unrelated sequence, for example a segment of the bacteriophage lambda sequence) are included.

The mastermix of the kit contains all required components, including enzymes but excluding magnesium ions. Magnesium is included in the kit, as a separate solution. After combining both kit solutions with the isolated nucleic acid from the sample, the mixture is used directly in the LightCycler instrument and data analysis is possible without any further sample treatment.

The internal control RNA, is included in the kit and provided in a separate solution. Optionally, it can be already included in the sample lysis step (to control nucleic acid extraction efficiency) or only later, it can be added to the mastermix (to control the efficiency of RT-PCR, only).

EXAMPLE 2

Quantitative Real Time RT-PCR for Detecting SARS-Associated Virus

The following is a specific protocol for quantitative real time RT-PCR for detecting SARS-associated virus:

RealArt™ HPA-Coronavirus LC RT PCR Reagents

Kit contents for use with the LightCycler™ Instrument (Roche Diagnostics).

Section 1. Kit Contents

TABLE 3

| Kit Contents of a kit for detection of SARS-associated virus | | | | |
|---|---|---|---|---|
| | Labelling and contents | Art. No. 5601-01 24 reactions | Art. No. 5601-02 48 reactions | Art. No. 5601-03 96 reactions |
| Blue | HPA-Coronavirus LC Master | 2 × 12 rxns | 4 × 12 rxns | 8 × 12 rxns |
| Yellow | HPA-Coronavirus LC Mg-Sol | 1 × 400 μl | 1 × 400 μl | 1 × 400 μl |
| Red | HPA-Coronavirus LC QS 1[¤] 1 × $10^4$ cop/μl | 1 × 200 μl | 1 × 200 μl | 1 × 200 μl |
| Red | HPA-Coronavirus LC QS 2[¤] 1 × $10^3$ cop/μl | 1 × 200 μl | 1 × 200 μl | 1 × 200 μl |
| Red | HPA-Coronavirus LC QS 3[¤] 1 × $10^2$ cop/μl | 1 × 200 μl | 1 × 200 μl | 1 × 200 μl |
| Red | HPA-Coronavirus LC QS 4[¤] 1 × $10^1$ cop/μl | 1 × 200 μl | 1 × 200 μl | 1 × 200 μl |

TABLE 3-continued Kit Contents of a kit for detection of SARS-associated virus

| | Labelling and contents | Art. No. 5601-01 24 reactions | Art. No. 5601-02 48 reactions | Art. No. 5601-03 96 reactions |
|---|---|---|---|---|
| Green | HPA-Coronavirus LC IC° | 1 × 1000 µl | 1 × 1000 µl | 1 × 1000 µl |
| White | Water (PCR grade) | 1 × 1000 µl | 1 × 1000 µl | 1 × 1000 µl |

°QS = Quantification Standard IC = Internal Control

Section 2. Storage

The kit components should be stored at −20° C. and are stable for 3 months at this temperature. Repeated thawing and freezing (>2×) should be avoided, as this may reduce the sensitivity. If the kit is to be used only intermittently, the reagents should be frozen in aliquots. Storage at +4° C. should not exceed a period of 5-6 hours.

Section 3. Additionally Required Materials and Devices

Disposable powder-free gloves; RNA isolation kit (described in 8.1 RNA Isolation); Physiological salt solution (0.9% NaCl) containing 1% N-Acetyl-cystein; Pipettes (adjustable 1-20 µl); Sterile pipette tips with aerosol barrier; Vortex mixer; Desktop centrifuge with rotor for 2 ml reaction tubes; LightCycler® Capillaries, (Roche Diagnostics); LightCycler® Cooling Block, (Roche Diagnostics); LightCycler® Instrument, (Roche Diagnostics).

Section 4. General Precautions for PCR

The user should always pay attention to the following: (1) Use pipette tips with filters (2) Storage of positive material (specimens, controls and amplicons) should be separated from all the other reagents and they should be added to the reaction mixes in a spatially separated facility. (3) Thaw all components thoroughly at room temperature before starting an assay. (4) When thawed, mix the components and centrifuge briefly. (5) Work quickly on ice or in the Cooling Block.

Section 5. Pathogen Information

Coronaviruses, a genus in the family Coronaviridae, are large enveloped, positive-stranded RNA viruses that cause highly virulent disease in humans and domestic animals. Two Coronaviruses that are known to infect humans cause one third of common colds and are also a common cause of health care-associated upper respiratory infections in premature infants.

A member of the Coronavirus family is considered to cause the Severe Acute Respiratory Syndrome (SARS). The virus is not classified yet. In the literature its suggested name is *Human Pneumonia-Associated Coronavirus* (HPAC). A part of a putative Coronavirus polymerase gene was identified via PCR in a SARS patient by the Bernhard Nocht Institute for Tropical Medicine in Hamburg and cooperating laboratories via PCR. This assay was used to establish a commercially available real time RT-PCR system for the direct detection of this new Coronavirus species.

Section 6. Principle of Real-Time PCR

Pathogen diagnosis by the polymerase chain reaction (PCR) is based on the amplification of specific regions of the pathogen genome. In real-time PCR, the amplified product is detected via fluorescent dyes. These are usually linked to oligonucleotide probes which bind specifically to the amplified product. Monitoring the fluorescence intensities during the PCR run (that is in real-time) allows the detection and quantification of the accumulating product without having to re-open the reaction tube after the PCR run.

Section 7. Product Description

The RealArt™ HPA-Coronavirus LC RT PCR Reagents constitutes a ready-to-use system for the detection of HPA-Coronavirus RNA using PCR in the LightCycler® Instrument (Roche Diagnostics). The HPA-Coronavirus LC Master contains reagents and enzymes for the specific amplification of a 80 bp region of the HPA-Coronavirus genome, and for the direct detection of the specific amplicon in fluorimeter channel F1 of the LightCycler® Instrument. In addition, the RealArt™ HPA-Coronavirus LC RT PCR Reagents contains a second heterologous amplification system to identify possible PCR inhibition. As an Internal Control (IC), it is detected in fluorimeter channel F3 and does not influence the analytical HPA-Coronavirus RT PCR. External positive controls (HPA-Coronavirus LC QS 1-4) are supplied which allow the determination of the pathogen load. For further information, refer to section 8.3 Quantification.

Section 8. Protocol

Section 8.1 RNA Isolation

Various manufacturers offer RNA isolation kits. Sample volumes for the RNA isolation procedure depend on the protocol used. RNA isolation is carried out according to the manufacturer's instructions. The following isolation kits are recommended (Table 4):

TABLE 4

Exemplary isolation kits

| Nucleic acid isolation kit | Catalogue number | Manufacturer |
|---|---|---|
| QIAamp UltraSens Virus Test Kit (50) | 53 704 | QIAGEN |
| QIAamp Viral RNA Mini Kit | 52 904 | QIAGEN |

It is important to use native provoced sputum (like MTB). Mix the sputum sample 1 to 2 for 30 min in physiological salt solution (0.9% NaCl) containing 1% N-Acetylcystein. Pellet the cells (ca. 600 µl) in a benchtop centrifuge (10000 g). Take 140 µl of the supernatant and the respective cell pellet in parallel (QIAamp viral RNA Mini Kit), add 560 µl AVL and go on with the ordinary viral RNA Protocol.

The RealArt™ HPA-Coronavirus LC RT PCR Reagents should not be used with phenol-based isolation methods. If the selected isolation kit does not contain carrier DNA/RNA, note that the addition of carrier RNA [RNA-Homopolymer Poly(A), Amersham Biosciences] at a concentration of 10 µg/ml lysis buffer to the sample/lysis buffer mixture is strongly recommended for nucleic acid isolation. When using isolation protocols with ethanol-containing washing buffers, carry out an additional centrifugation step before the elution to remove any remaining ethanol. This prevents possible inhibition of PCR.

Section 8.2 Internal Control

An Internal Control (HPA-Coronavirus LC IC) is supplied. The Internal Control of the RealArt™ HPA-Coronavirus LC RT PCR Reagents can be used directly in the isolation procedure. This allows the user both to control the isolation procedure and to check for possible PCR inhibition. For this application, add the Internal Control to the isolation at a ratio of 0.1 µl per 1 µl elution volume. For example, using the QIAamp Viral RNA Mini Kit, the RNA is eluted in 50 µl AE buffer. Hence, 5 µl of the Internal Control should be added initially. If, for example, the RNA is eluted in 100 µl, then use the corresponding volume of 10 µl. The quantity of IC used depends only on the elution volume. The Internal Control should be added directly to the sample/lysis buffer mixture. If RNA isolation from a larger number of specimens is required, then the Internal Control can be added directly to the lysis buffer.

The IC can optionally be used exclusively for checking for possible PCR inhibition. For this application, add 0.5 µl of the IC and 3 µl HPA-Coronavirus LC Mg-Sol per test mixture directly to 12 µl HPA-Corona-virus LC Master. For each PCR reaction, use 15 µl of the Master Mix produced as described above. (The volume increase caused by adding the IC is neglected when preparing the PCR assay. The sensitivity of the detection system is not impaired.) Then 5 µl of the purified sample is added. If several samples are being prepared for a PCR run, increase the volume of the HPA-Coronavirus LC Master, HPA-Coronavirus LC Mg-Sol and the Internal Control according to the number of samples (see Section 8.4 Preparing the PCR).

Section 8.3 Quantification

The enclosed quantification standards (HPA-Coronavirus LC QS 1-4) are treated as previously purified samples and the same volume is used (5 µl). To generate a standard curve in the LightCycler® Instrument, all 4 quantification controls should be used and defined in the Sample Loading Screen as standards with the specified concentrations (see LightCycler Operator's Manual, Version 3.5, Chapter B, 2.4. Sample Data Entry). The standard curve generated as above can also be used for subsequent runs, provided that at least one standard is used in the current run. For this purpose, the previously generated standard curve needs to be imported (see LightCycler Operator's Manual, Version 3.5, Chapter B, 4.2.5. Quantification with an External Standard Curve). However, this quantification method may lead to deviations in the results due to variabilities between different PCR runs.

The quantification controls are defined as copies/µl. The following formula is to be applied to convert the values determined using the standard curve into copies/ml of sample material:

$$\text{Result (copies/ml)} = \frac{\text{Result (copies/µl)} \times \text{Elution Volume (µl)}}{\text{Sample Volume (ml)}}$$

Section 8.4 Preparing the PCR

Make sure that the Cooling Block as well as the capillary adapters (accessories of the LightCycler® Instrument) are pre-cooled to +4° C. Place the desired number of LightCycler® capillaries into the adapters of the Cooling Block. Use at least one quantification standard as well as one negative control (water, PCR grade) are included per PCR run. To generate a standard curve, use all supplied quantification standards (HPA-Coronavirus LC QS 1-4) for each PCR run. Before each use, all reagents need to be thawed completely and mixed (by repeated up and down pipetting or by brief vortexing).

If it is desired to use the Internal Control to check not only possible PCR inhibition but also the isolation procedure, the IC has already been added to the isolation (see Section 8.2 Internal Control). In this case, use the following pipetting scheme (Table 5)(for a schematic overview see FIG. 1)(for FIG. 1, Addition of the Internal Control into the Purification Procedure. Check that the solutions are thawed completely, mixed well and centrifuged briefly.):

TABLE 5

Protocol for assay preparation for use of internal control for PCR inhibition and isolation procedure

| | | Number of samples | |
|---|---|---|---|
| | | 1 | 12 |
| 1. Preparation of Master Mix | HPA-Coronavirus LC Master | 12 µl | 144 µl |
| | HPA-Coronavirus LC Mg-Sol | 3 µl | 36 µl |
| | HPA-Coronavirus LC IC | 0 µl | 0 µl |
| | Total volume | 15 µl | 180 µl |
| 2. Preparation of PCR assay | Master Mix | 15 µl | 15 µl each |
| | Sample | 5 µl | 5 µl each |
| | Total volume | 20 µl | 20 µl each |

Figure 2:
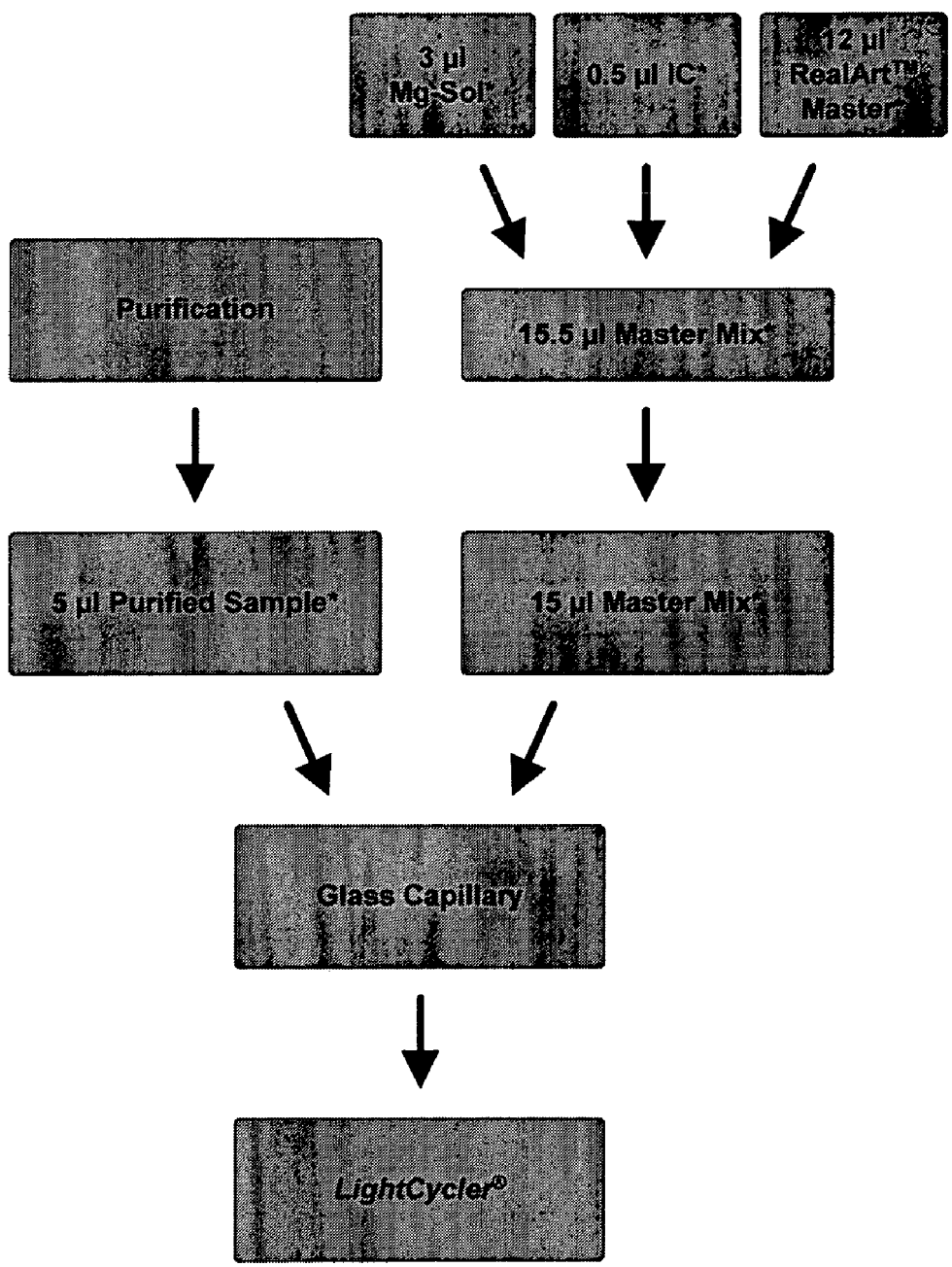
FIG. 2 shows a schematic workflow for the control of PCR inhibition

If it is desired to use the IC exclusively for checking for PCR inhibition, it must be added directly to the HPA-Coronavirus LC Master. In this case, use the following pipetting scheme (Table 6)(for a schematic overview see FIG. 2)(for FIG. 2., Check that the solutions are thawed completely, mixed well and centrifuged briefly. Addition of the Internal Control into the RealArt™ Master).

TABLE 6

Protocol for assay preparation for use of internal control for PCR inhibition.

| | | Number of samples | |
|---|---|---|---|
| | | 1 | 12 |
| 1. Preparation of Master Mix | HPA-Coronavirus LC Master | 12 µl | 144 µl |
| | HPA-Coronavirus LC Mg-Sol | 3 µl | 36 µl |
| | HPA-Coronavirus LC IC | 0.5 µl | 6 µl |
| | Total volume | 15.5 µl | 186 µl |
| 2. Preparation of PCR assay | Master Mix | 15 µl♦ | 15 µl each♦ |
| | Sample | 5 µl | 5 µl each |
| | Total volume | 20 µl | 20 µl each |

♦The volume increase caused by adding the IC is neglected when preparing the PCR assay. The sensitivity of the detection system is not impaired.

Pipette 15 µl of the Master Mix into the plastic reservoir of each capillary. Then add 5 µl of the eluated sample RNA to each tube. Correspondingly, 5 µl of at least one of the quantification standards (HPA-Coronavirus LC QS 1 4) must be used as a positive control and 5 µl of water (PCR grade) as a negative control. Close the capillaries. To transfer the mixture from the plastic reservoir of the capillary into the glass tube, centrifuge the adapters containing the capillaries in a desktop centrifuge for 10 seconds at a maximum of 400×g (2000 rpm).

Section 8.5 Programming of the LightCycler™ Instrument

Figure 3:
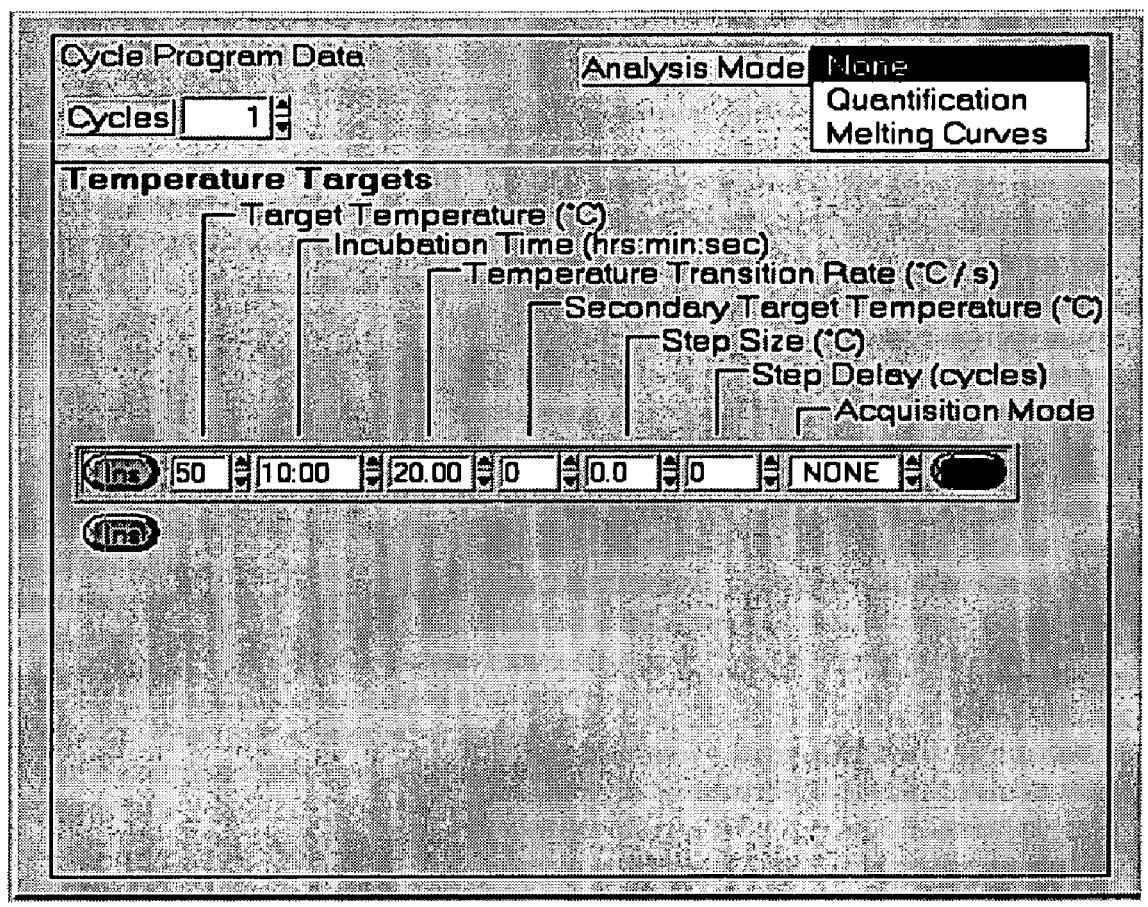
FIG. 3 shows a protocol for reverse transcription of the RNA.
Figure 4:
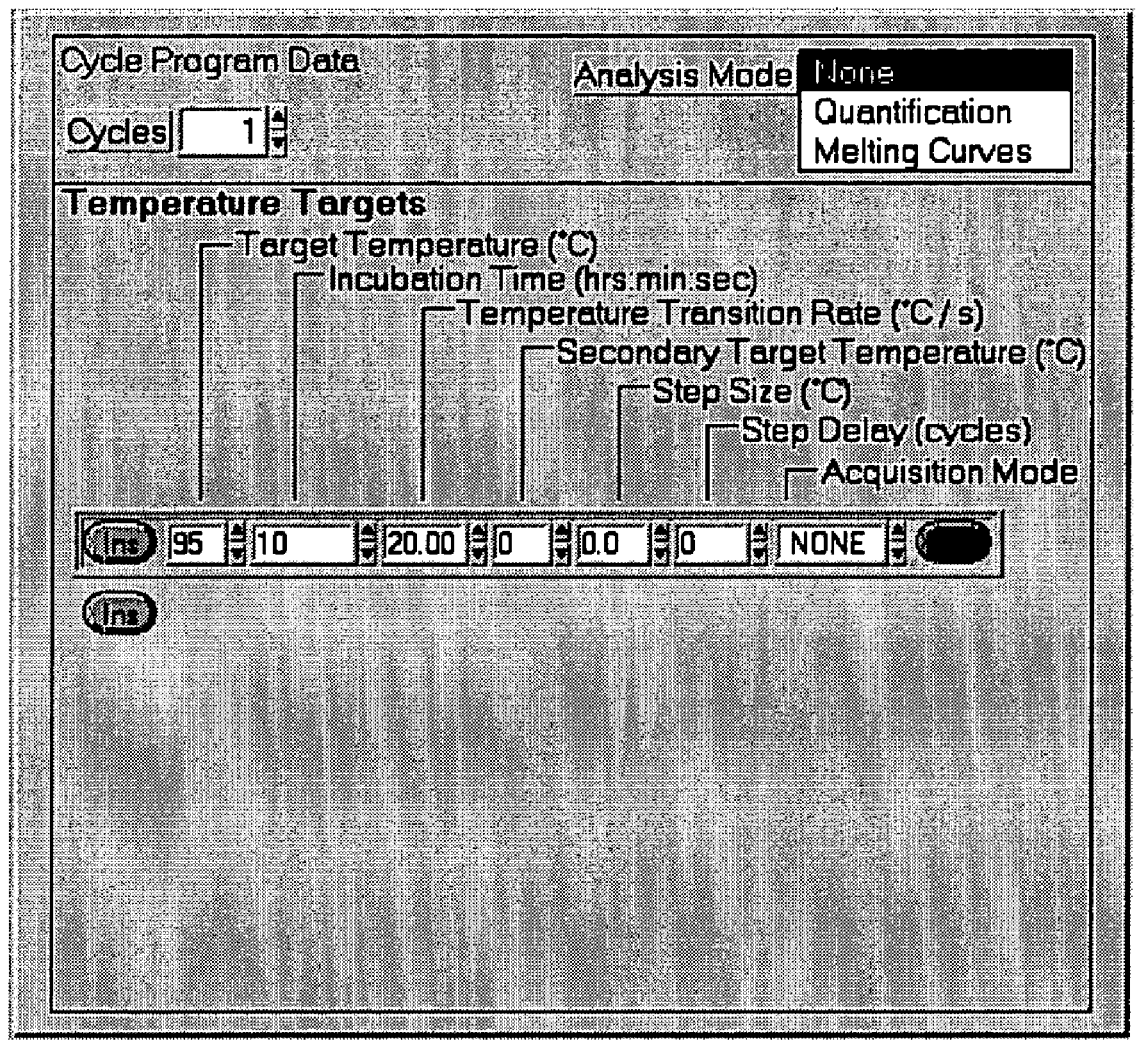
FIG. 4 shows a protocol for initial activation of the Hot Start enzyme.
Figure 5:
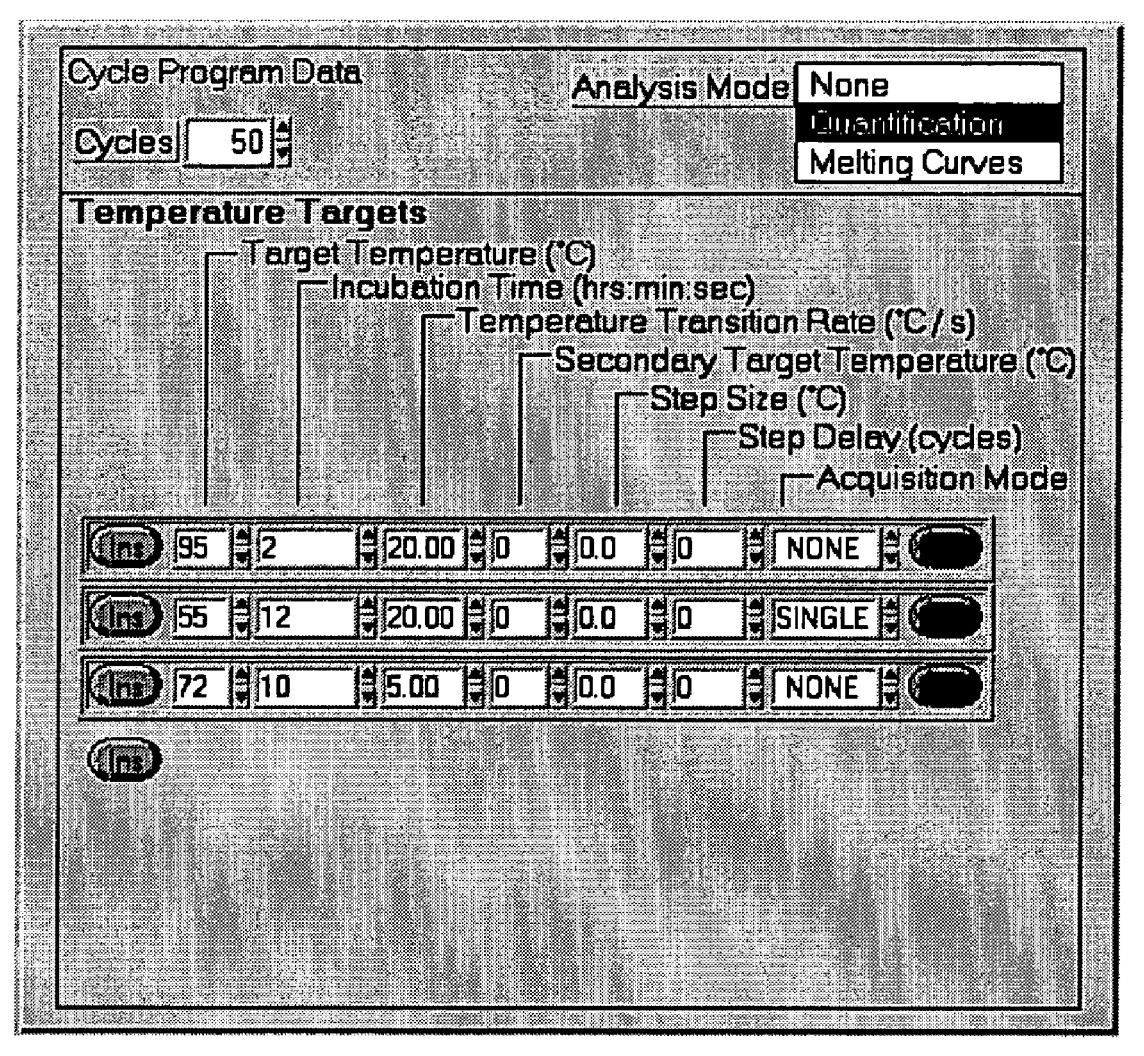
Figure 6:
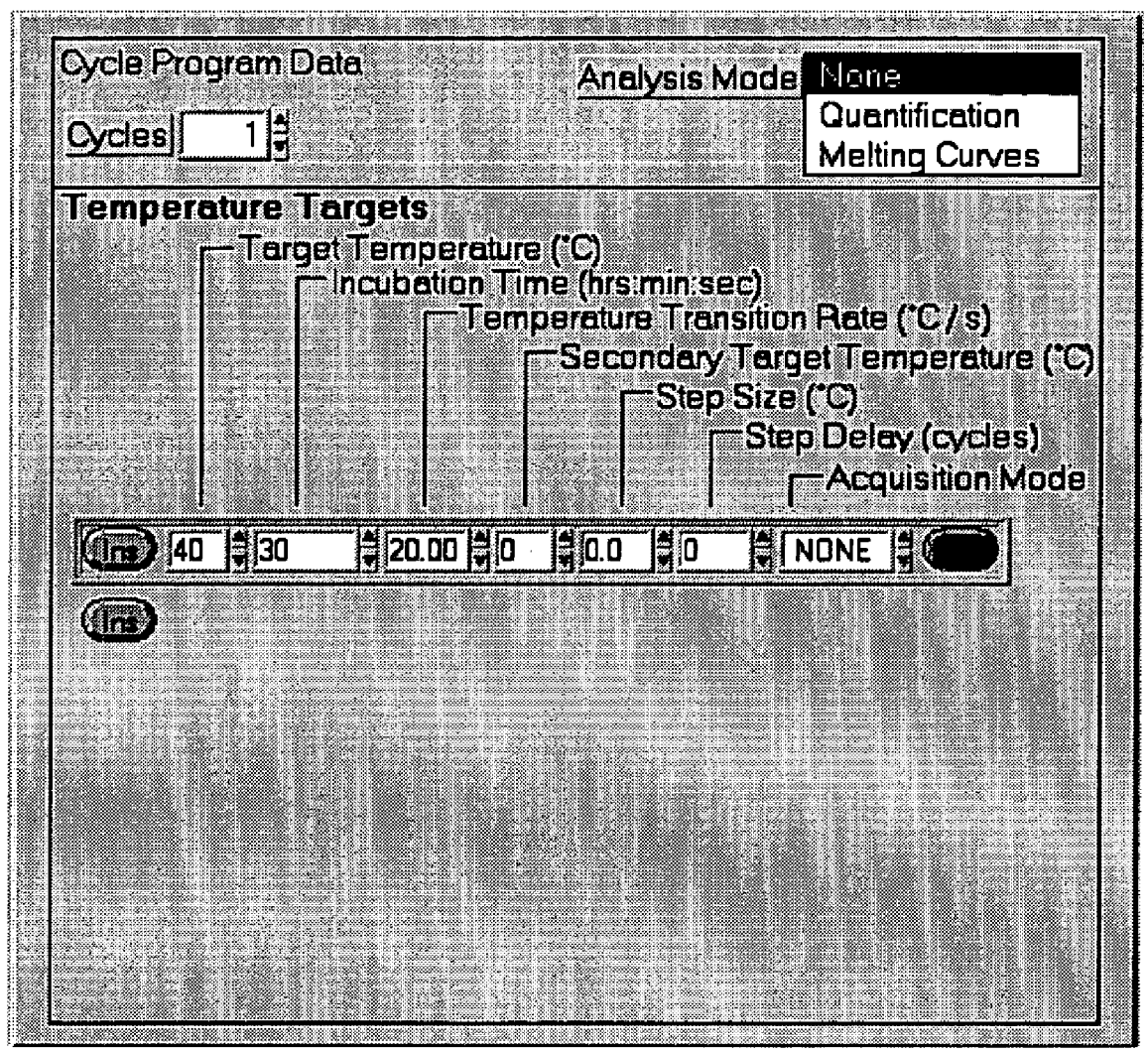
FIG. 6 shows a protocol for cooling.

The LightCycler® PCR program for the detection of HPA-Coronavirus RNA can be divided into 4 steps: (A) Reverse transcription of the RNA (FIG. 3); (B) Initial activation of the Hot Start enzyme (FIG. 4); (C) Amplification of the cDNA (FIG. 5); (D) Cooling (FIG. 6)

Program the LightCycler® Instrument for these 4 steps according to the parameters shown in FIGS. 3-6. Pay particular attention to the settings for Analysis Mode, Cycle Program Data and Temperature Targets. In the illustrations these settings are framed in bold black. Find further information on programming the LightCycler® Instrument in the LightCycler Operator's Manual.

Section 9. Data Analysis

In multicolour analysis, interferences occur between fluorimeter channels. The LightCycler® Instrument's software contains a file termed Colour Compensation File, which compensates for this interference. Open this file during or after the PCR run by activating the Choose CCC File or the Select CC Data button. If no Colour Compensation File is installed, generate the file according to the instructions in the LightCycler Operator's Manual. After the Colour Compensation File has been activated, separate signals for the analytical HPA-Coronavirus RT PCR (F1/F2) and for the Internal Control (F3/Back-F1) appear in fluorimeter channels F1 and F3. (When using older software versions (version 3.3 and older) the display option F3/Back F1 is not available. In this case, select F3/F1 to display the Internal Control). For the analysis of quantitative runs, follow the instructions given in Section 8.3 Quantification.

The following results are possible:

(1) A signal is detected in the fluorimeter channel F1/F2. The result of the analysis is positive: The sample contains HPA-Coronavirus RNA. In this case, the detection of a signal in the F3/Back-F1 channel is dispensable, since high initial concentrations of HPA-Coronavirus RNA (positive signal in the F1/F2 channel) can lead to a reduced or absent fluorescence signal of the Internal Control in the F3/Back-F1 channel (competition).

(2) In fluorimeter channel F1/F2, no signal is detected. At the same time, a signal from the Internal Control appears in the F3/Back-F1 channel. The sample contains no detectable HPA-Coronavirus RNA and can be considered negative. In the case of a negative HPA-Coronavirus RT PCR, the detected signal of the IC rules out the possibility of PCR inhibition.

(3) No signal is detected in F1/F2 or in the F3/Back-F1 channel. In this case, no diagnosis can be concluded. Information regarding error sources and their solution can be found in Section 10 Troubleshooting.

Figure 7:
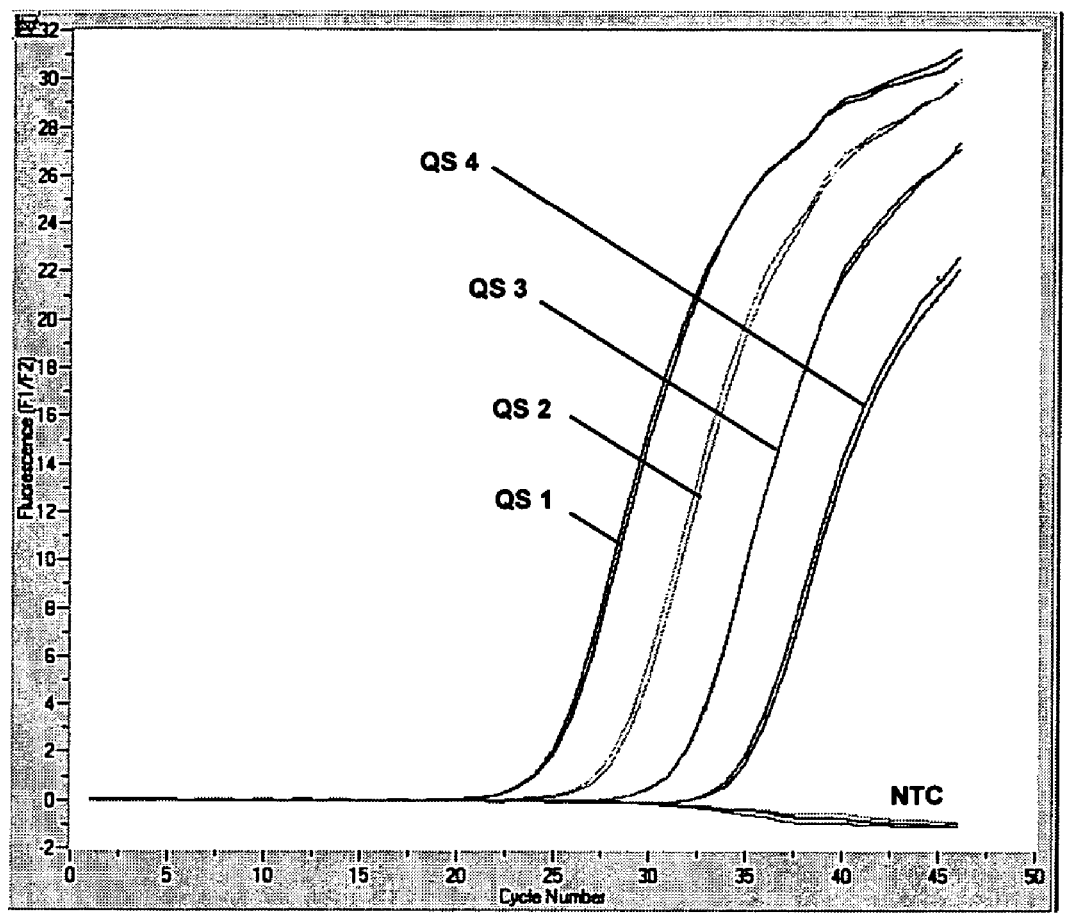
FIG. 7 shows detection of the quantification standards (HPA-Coronavirus LC QS 1-4) in fluorimeter channel F1/F2. NTC: non-template control.
Figure 8:
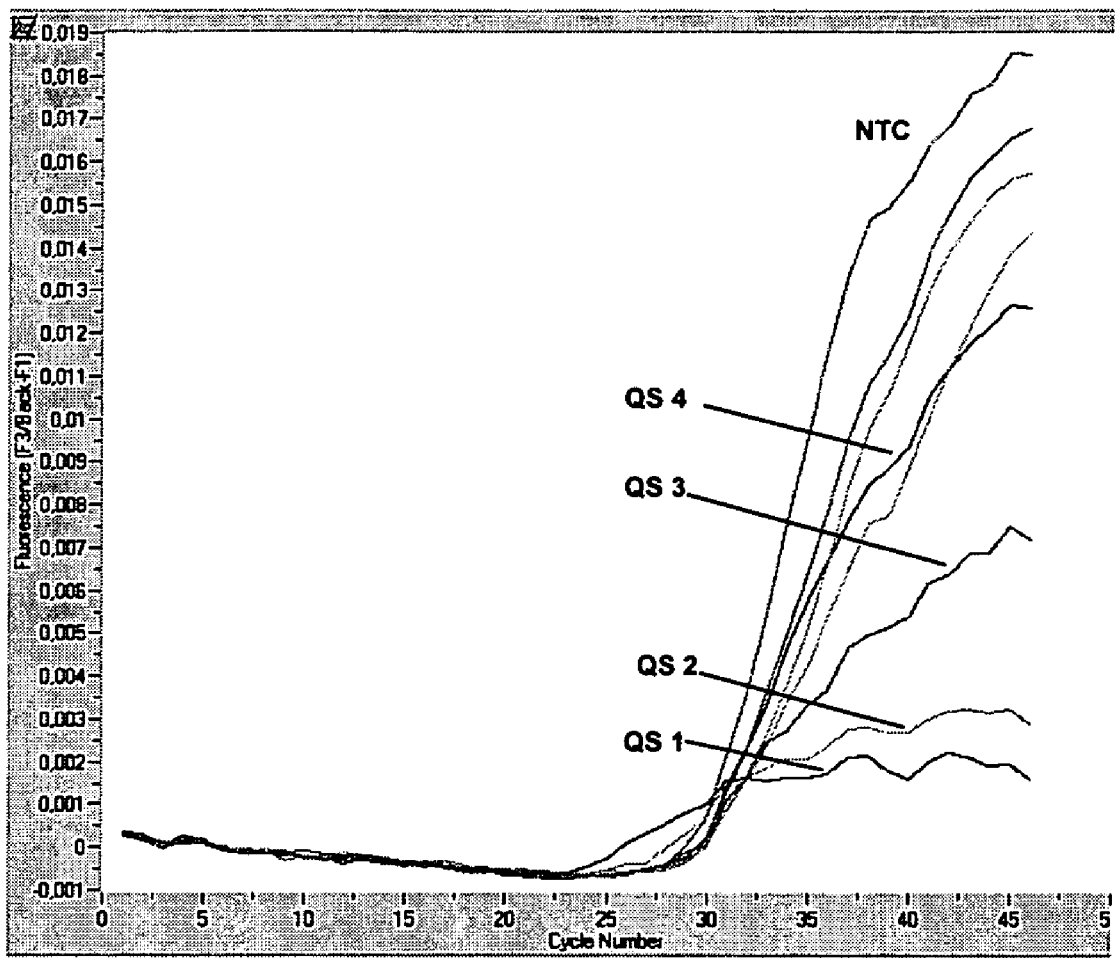
FIG. 8 shows detection of the Internal Control (IC) in fluorimeter channel F3/Back-F1 in parallel with a simultaneous amplification of quantification standards (HPA-Coronavirus LC QS 1-4). NTC is non-template control.
Figure 10A:
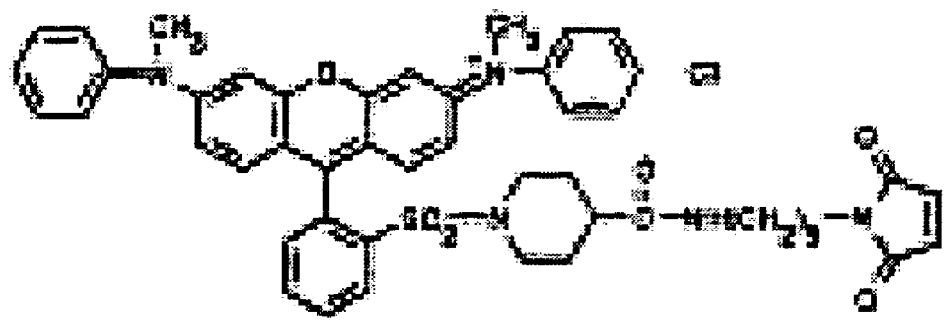
FIG. 10A shows QSY-7 (QSY-7-Maleimide) (Molecular Probes).
Figure 10B:
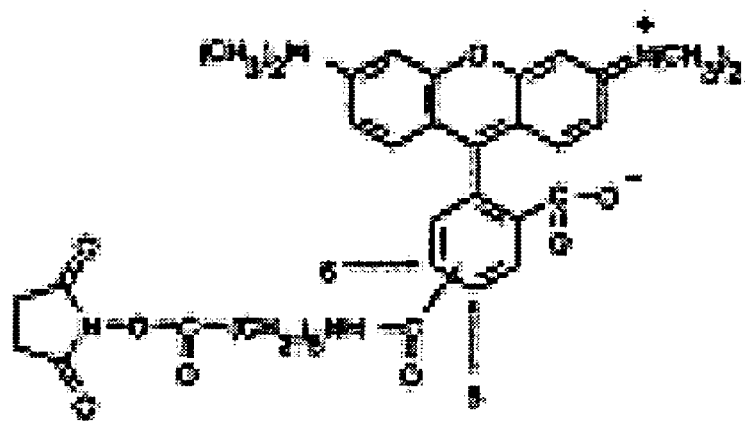
FIG. 10B shows TAMRA: 6-(tetramethylrhodamine-5 (and 6) carboxyamido)hexanoic acid succinimidyl ester (5(6)-TAMRA-X SE) (Molecular Probes).
Figure 10C:
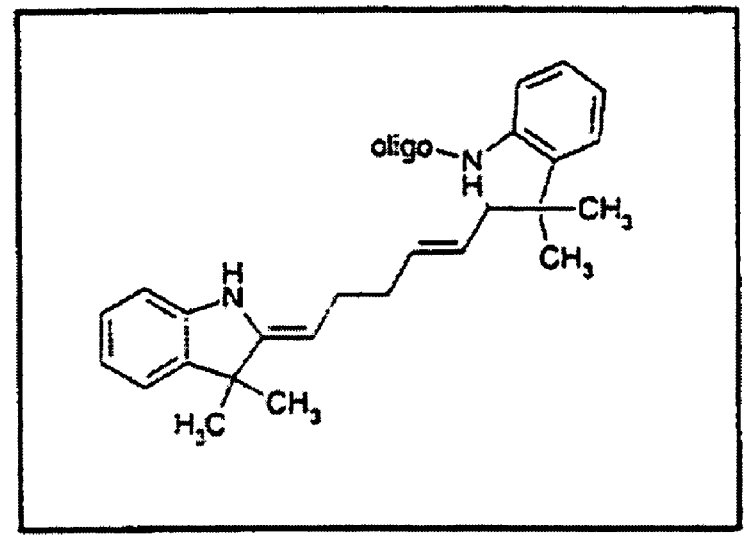
FIG. 10C-10N show representative reporter/quencher fluorescent dyes.
Figure 10D:
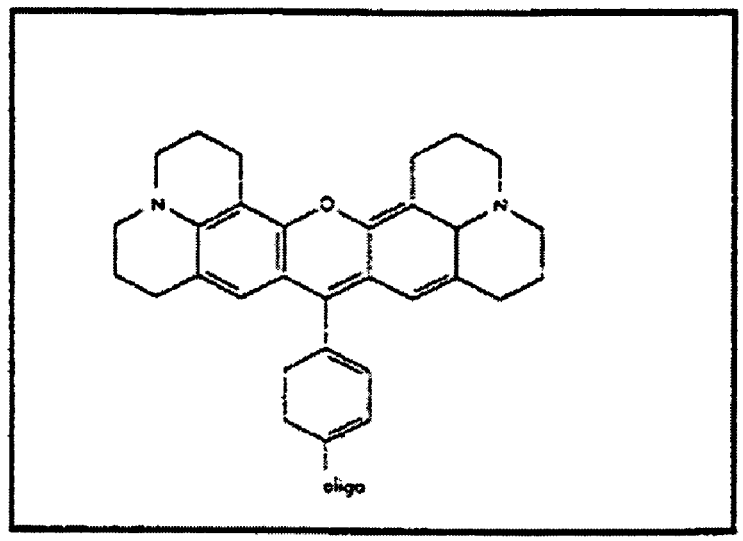
Figure 10E:
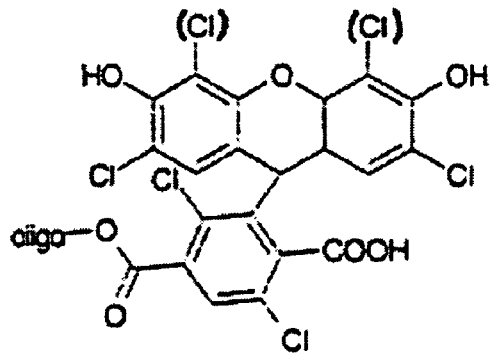
Figure 10F:
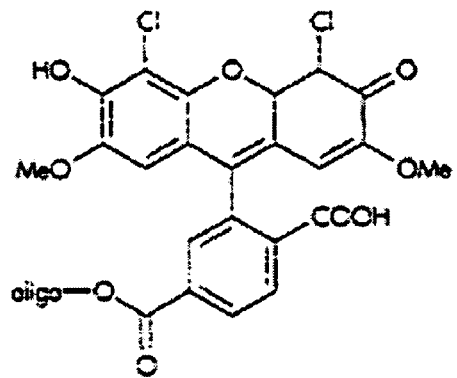
Figure 10G:
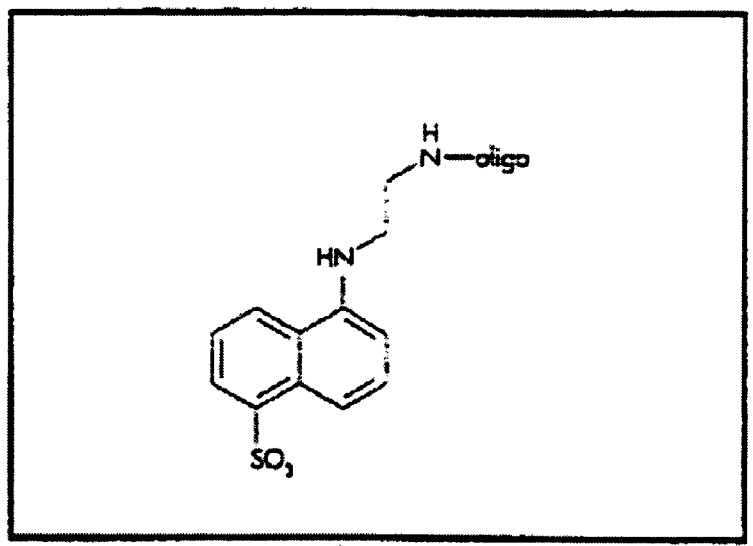
Figure 10H:
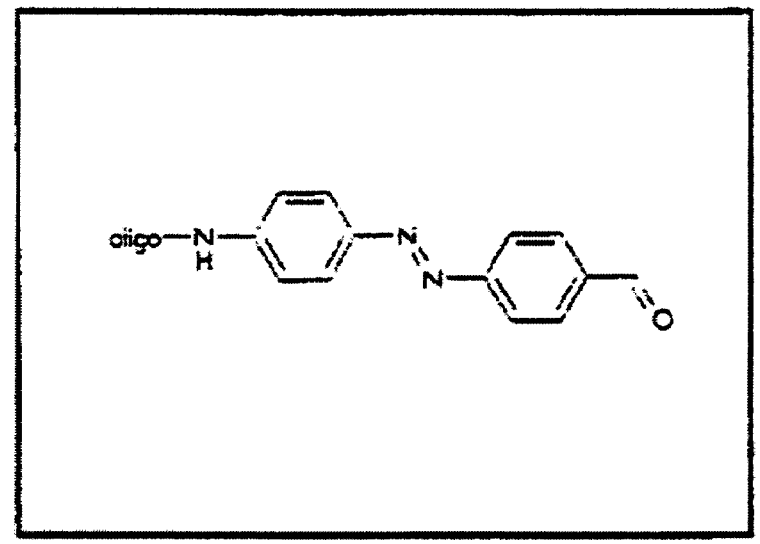
Figure 10I:
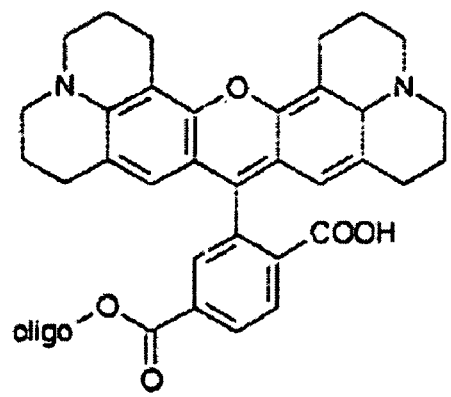
Figure 10J:
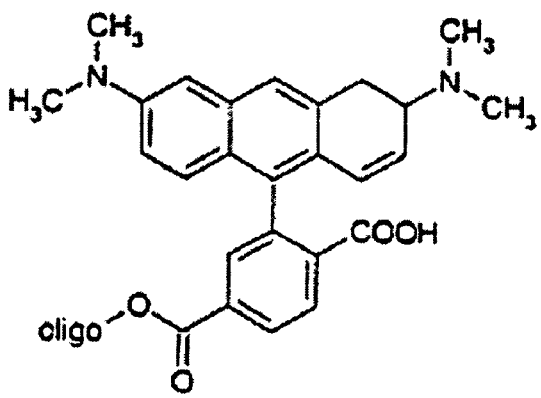
Figure 10K:
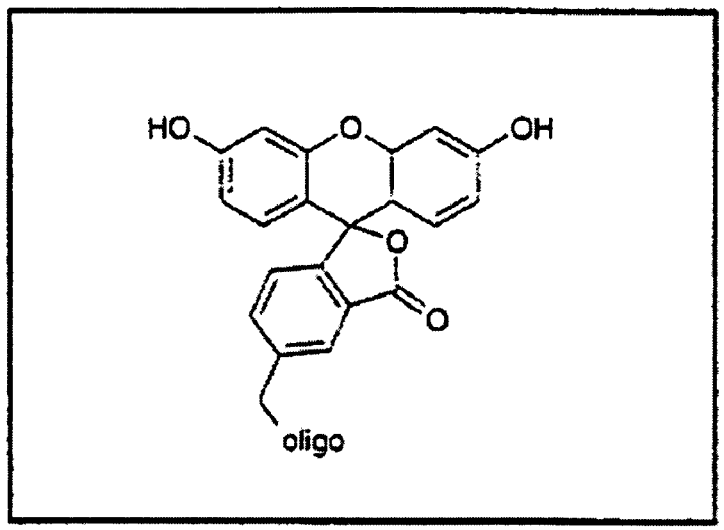
Figure 10L:
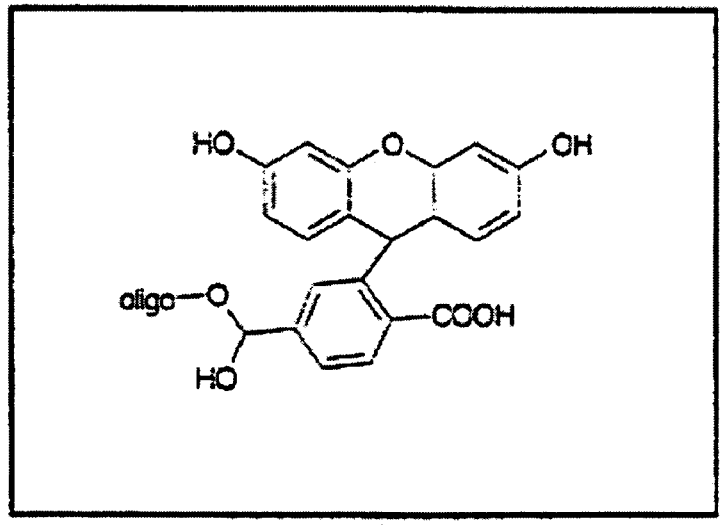
Figure 10M:
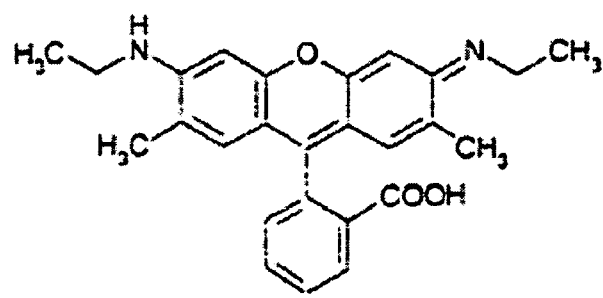
Figure 10N:
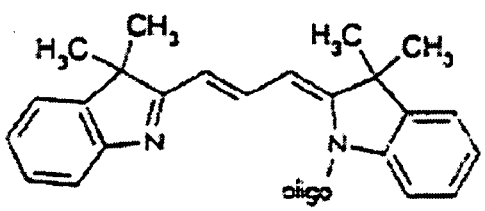

Examples of positive and negative PCR reactions are given in FIGS. 7 and 8.

Section 10. Troubleshooting (1) No signal with positive controls (HPA-Coronavirus LC QS 1 4) in fluorimeter channel F1/F2:
  (a) Incorrect programming of the LightCycler® Instrument Solution: repeat the PCR with corrected settings.

(2) Weak or no signal of the Internal Control in fluorimeter channel F3/Back-F1 and simultaneous absence of a signal in channel F1/F2:
  (a) The PCR conditions do not comply with the protocol. Solution: repeat the PCR with corrected settings.
  (b) The HPA-Coronavirus LC Master has been thawed and frozen too often.
  (c) The HPA-Coronavirus LC Master has been kept at +4° C. for longer than 56 hours.

Solution: Mind the storage conditions given in Section 2, Storage. Repeat the PCR using a new HPA-Coronavirus LC Master.

(d) The PCR was inhibited. Solution: Make sure that a recommended isolation method is used (see 8.1 RNA Isolation) and stick closely to the manufacturer's instructions.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention. Accordingly, the invention is limited only by the claims.

I claim:

1. A kit for detecting Severe Acute Respiratory Syndrome-associated virus (SARS-associated virus), named HPAC (Human Pneumonia-Associated Coronavirus), comprising
   a forward primer that is 18 to 31 nucleotides in length and binds to a region defined by nucleotides 69 to 98 of the sequence shown as SEQ ID NO:1;
   a reverse primer that is 18 to 31 nucleotides in length and binds to a region defined by nucleotides 123 to 168 of the sequence shown as SEQ ID NO:1; and
   a probe that is 18 to 35 nucleotides in length, binds to a region defined by nucleotides 89 to 132 of the sequence shown as SEQ ID NO:1, and is labeled with a fluorescent reporter dye, and a quencher dye, wherein the forward and reverse primers are capable of amplifying a nucleic acid fragment using SEQ ID NO:1 and its complement as templates, and the probe is capable of detecting the presence of the amplified nucleic acid fragment.

2. The kit according to claim 1, wherein the forward primer has the sequence shown as SEQ ID NO:2, the reverse primer has the sequence shown as SEQ ID NO:3, and the probe has the sequence shown as SEQ ID NO:4 .

3. The kit according to claim 1, wherein the reporter dye is FAM, 6-FAM, 5-FAM or ALEXA-288.

4. The kit according to claim 1, wherein the quencher dye is TAMRA, DABCYL or QSY.

5. The kit according to claim 1, further comprising enzymes and reagents required for performing a real time RT-PCR reaction.

6. An isolated oligonucleotide that consists of 18, 19, 20, 21, 22, 23, 25, 26, 27, 28, 29, 30, or 31 nucleotides, and is capable of bindings to a region defined by nucleotides 69 to 98 of the sequence shown as SEQ ID NO:1 and being extended using the complement of SEQ ID NO:1 as a template, wherein the oligonucleotide binds the region at 55° C.

7. The isolated oligonucleotide according to claim 6, having the sequence shown as SEQ ID NO:2, wherein the oligonucleotide binds the region at 55° C.

8. An isolated oligonucleotide that consists of 18, 19, 21, 22, 23, 25, 26, 27, 28, 29, 30, or 31 nucleotides, and is capable of binding to a region defined by nucleotides 123 to 168 of the sequence shown as SEQ ID NO:1 and being extended using SEQ ID NO:1 as a template.

9. The isolated oligonucleotide according to claim 8, having the sequence shown as SEQ ID NO:3.

10. A kit for detecting Severe Acute Respiratory Syndrome-associated virus (SARS-associated virus), named HPAC (Human Pneumonia-Associated Coronavirus), comprising:

a forward primer that is 18 to 35 nucleotides in length, and binds to a region defined by nucleotides about 1 to about 240 of the sequence shown as SEQ ID NO:1.

a reverse primer that is 18 to 35 nucleotides in length, and binds to a region defined by nucleotides about 60 to about 300 of the sequence shown as SEQ ID NO:1; and a probe that is 12 to 40 nucleotides in length, binds to a region defined by nucleotides about 21 to about 279 of the sequence shown as SEQ ID NO:1, and is labeled with a fluorescent reporter dye and a quencher dye;

wherein the forward and reverse primers amplify a nucleic acid fragment using SEQ ID NO:1 and its complement as templates, and the probe detects the presence of the amplified nucleic acid fragment.

11. A method for detecting Severe Acute Respiratory Syndrome-associated virus (SARS-associated virus), named HPAC (Human Pneumonia-Associated Coronavirus), comprising:

contacting a biological sample with the forward primer, the reverse primer and the probe of the kit of claim 10, incubating under conditions allowing amplification of nucleic acid using said forward and reverse primers, and determining binding of said probe to the amplified nucleic acid, wherein detecting binding of said probe to the amplified nucleic acid indicates the presence of SARS-associated virus in the biological sample.

12. The method of claim 11, wherein the amplification and detection are performed using real time RT-PCR.

13. The method of claim 11, wherein the forward primer has the sequence shown as SEQ ID NO:2, the reverse primer has the sequence shown as SEQ ID NO:3, and the probe has the sequence shown as SEQ ID NO:4.

14. The method of claim 11, wherein the reporter dye is FAM, 6-FAM, 5-FAM or ALEXA-288.

15. The method of claim 11, wherein the quencher dye is TAMRA, DABCYL or QSY.

16. The method of claim 11, wherein the detection is quantitative detection of the real time fluorescence signal intensity.

17. The method of claim 11, wherein the biological sample is a body fluid.

18. The method of claim 11, wherein the biological sample is sputum, feces or blood.

19. An oligonucleotide that is 9-20 nucleotides in length, capable of binding to a region defined by nucleotides 69 to 98 of the sequence shown as SEQ ID NO:1 and being extended using the complement of SEQ ID NO:1 as a template, and isolated as a single species of molecule, wherein the oligonucleotide binds the region at 55° C.

20. The oligonucleotide according to claim 19, wherein the oligonucleotide comprises the sequence shown as SEQ ID NO:2.

21. An oligonucleotide that is 9-20 nucleotides in length, capable of binding to a region defined by nucleotides 123 to 168 of the sequence shown as SEQ ID NO:1 and being extended using SEQ ID NO:1 as a template, and isolated as a single type of molecule, wherein the oligonucleotide binds the region at 55° C.

22. The oligonucleotide according to claim 21, wherein the oligonucleotide comprises the sequence shown as SEQ ID NO:3.

* * * * *

UNITED STATES PATENT AND TRADEMARK OFFICE
CERTIFICATE OF CORRECTION

PATENT NO. : 7,374,883 B2
APPLICATION NO. : 10/837026
DATED : May 20, 2008
INVENTOR(S) : Thomas Laue Page 1 of 1

It is certified that error appears in the above-identified patent and that said Letters Patent is hereby corrected as shown below:

On Title Page
Item (56) References Cited, 5$^{th}$ source, "repiratory" should read as --respiratory--.

Column 15
Lines 52-53, "are capable of amplifying" should read as --amplify--.
Lines 54-55, "is capable of detecting" should read as --detects--.

Column 16
Line 39, "bindings" should read as --binding--.

Lines 44-46, claim 7, should correctly read as --7. The isolated oligonucleotide according to claim 6, having the sequence shown as SEQ ID NO:2.--.

Lines 47-51, claim 8, should correctly read as --8. An isolated oligonucleotide that consists of 18, 19, 20, 21, 22, 23, 25, 26, 27, 28, 29, 30, or 31 nucleotides, and is capable of binding to a region defined by nucleotides 123 to 168 of the sequence shown as SEQ ID NO:1 and being extended using SEQ ID NO:1 as a template, wherein the oligonucleotide binds the region at 55° C.--.

Line 60, Delete period "." should read as --;--.

Column 18
Line 8, "9-20" should read as --18-31--.
Line 17, "9-20" should read as --18-31--.

Signed and Sealed this

Seventh Day of October, 2008

JON W. DUDAS
*Director of the United States Patent and Trademark Office*